United States Patent [19]

Sakai et al.

[11] Patent Number: 4,502,320
[45] Date of Patent: Mar. 5, 1985

[54] METHOD AND APPARATUS FOR DIAGNOSING OIL-FILLED ELECTRIC APPARATUS

[75] Inventors: Seiichi Sakai, Kagawa; Toshihiko Gange, Takamatsu; Hideo Tsukioka, Mito; Katuo Sugawara, Hitachi; Ichitaro Tani, Kitaibaraki; Etsunori Mori; Shigeo Shiono, both of Hitachi, all of Japan

[73] Assignees: Hitachi, Ltd.; Shikoku Electric Power Company, Inc., both of Tokyo, Japan

[21] Appl. No.: 400,157

[22] Filed: Jul. 20, 1982

[30] Foreign Application Priority Data

Jul. 27, 1981 [JP] Japan ................. 56-117927

[51] Int. Cl.³ .......................................... G01N 31/00
[52] U.S. Cl. .......................................... 73/23; 73/19
[58] Field of Search ............... 73/19, 23; 364/497, 364/498, 499; 340/646

[56] References Cited

U.S. PATENT DOCUMENTS 4,148,086 4/1979 Landa et al. ................. 340/646
4,236,404 12/1980 Ketchum et al. ............. 73/19
4,402,211 9/1983 Sugawara et al. ........... 73/19

FOREIGN PATENT DOCUMENTS 1397935 6/1975 United Kingdom .

OTHER PUBLICATIONS

International Electrotechnical Commission, Publication No. 599, "Inter. of Anal. of Gases in Transformers and other Oil-Filled Elec. Equip.", pp. 3-25(odd pages), Nov. 1977.

Primary Examiner—Stephen A. Kreitman
Attorney, Agent, or Firm—Antonelli, Terry & Wands

[57] ABSTRACT

Method and apparatus for diagnosing abnormality of an oil-filled electric apparatus is disclosed. Presence or absence of abnormality is determined by comparing contents of plural predetermined components contained in gas extracted from the oil of the electric apparatus with respective predetermined reference values. The type of abnormality is determined on the basis of at least one set of two specific components selected from the plural components.

25 Claims, 9 Drawing Figures

METHOD AND APPARATUS FOR DIAGNOSING OIL-FILLED ELECTRIC APPARATUS

The present invention relates generally to a method and apparatus for diagnosing abnormality of an oil-filled electric apparatus. In particular, the invention concerns a method of automatically diagnosing thermal and/or electrical abnormality taking place in the oil-filled electric apparatus by detecting various gas components contained in a gas extracted from the oil and an apparatus for carrying out the method.

As a hitherto known method of diagnosing abnormality of the oil-filled electric apparatus such as oil transformer, oil reactor and the like, it is known to determine the occurrence or non-occurrence of abnormality of the apparatus by detecting concentrations or increases in contents of various gas components contained in the oil and to analyze the type of abnormality on the basis of ratios in content between specific gas components. More particularly, an in-oil gas extractor operative on the principle of Torricellian vacuum, an in-oil gas extractor employing a Toepler pump, an in-oil gas extractor constituted by a reciprocating piston or an in-oil gas separating film made of an inorganic or organic material is mounted to the oil-filled electric apparatus such as the oil transformer, wherein gases trapped are analyzed through gas chromatograph or by means of a combustion type gas sensor thereby to determine the presence or absence of the internal abnormality of the oil-filled electric apparatus on the basis of the total amount of the gas components or amounts of the individual gas components such as $H_2$, $CO$, $CH_4$, $C_2H_2$, $C_2H_4$, $C_2H_6$ and others or the degree of increasing in the amount of each gas component and/or the type of the abnormality by encoding the ratios of $CH_4/H_2$, $C_2H_2/C_2H_4$, $C_2H_4/C_2H_6$ and the like and comparing a combination of the encoded ratios with a previously prepared code table which are experimentally prepared for various abnormalities of different types.

The judging of abnormality through such manual processing as described above necessarily takes a lot of time. Under the circumstance, there exists a great demand for a method and an apparatus which make it possible to judge rapidly abnormality of the oil-filled electric apparatus with accuracy in a facilitated manner.

It is an object of the present invention to provide a method which is evaded from the shortcomings described above and is capable of automatically and rapidly determining the presence or absence of internal abnormality in oil-filled electric apparatus and also the type of abnormality, if present, with high accuracy and reliability in a simplified manner.

Another object of the present invention is to provide an automatic diagnosis apparatus for automatically carrying out the method described above.

According to the invention, there is provided a method of diagnosing an oil-filled electric apparatus by detecting contents of plural predetermined components contained in gas extracted from oil of said electric apparatus, said components bearing relevance to abnormality of said electric apparatus due to electric discharge and overheat; determining the presence or absence of abnormality due to electric discharge or overheat by comparing the contents of said gas components with respective reference values; and determining ratio of contents for at least one set of two selected components among those detected, when the abnormality has been detected, and determining on the basis of the value of said ratio whether said abnormality is due to overheat or discharge.

According to another aspect of the invention, there is provided an apparatus for carrying out the above method which comprises first means receiving signals representing contents of plural predetermined components contained in gas extracted from oil of said electric apparatus, said components bearing relevance to abnormality of said electric apparatus due to electric discharge and overheat; second means for determining the presence or absence of abnormality due to discharge or overheat by comparing the contents of said gas components with respective reference values; and third means for obtaining ratio of contents for at least one set of two specific components among said components, when the abnormality has been detected, thereby to determine on the basis of the value of said ratio whether said abnormality is due to overheat or discharge.

The above and other objects, features and advantages of the present invention will be more clearly understood from the following description of embodiments of the invention with reference to the accompanying drawings, in which.

Figure 4:
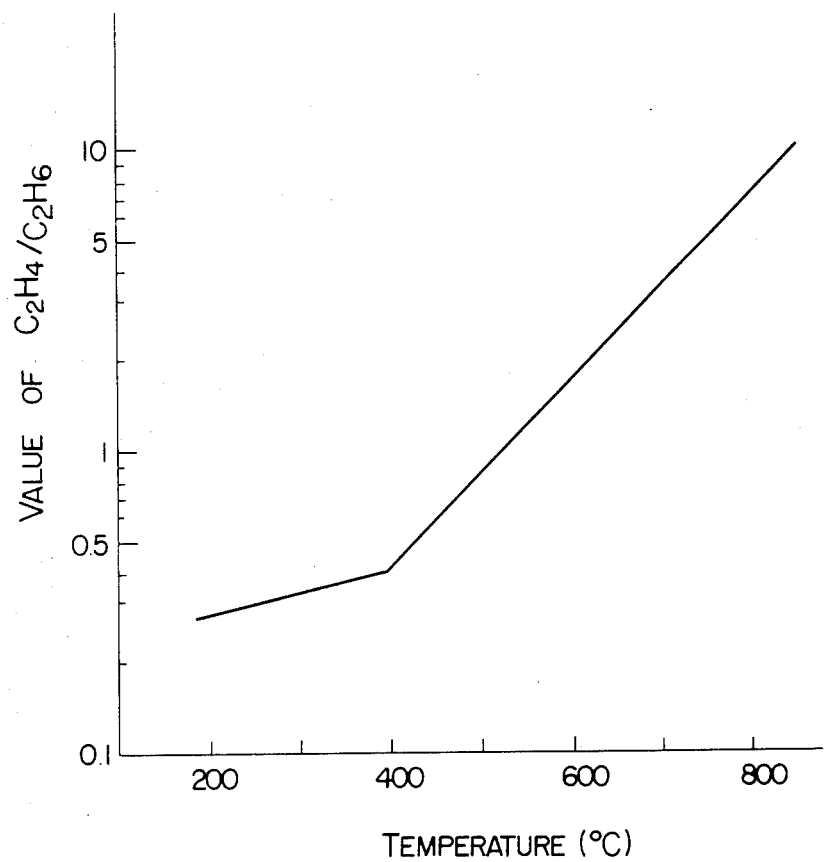
Figure 5:
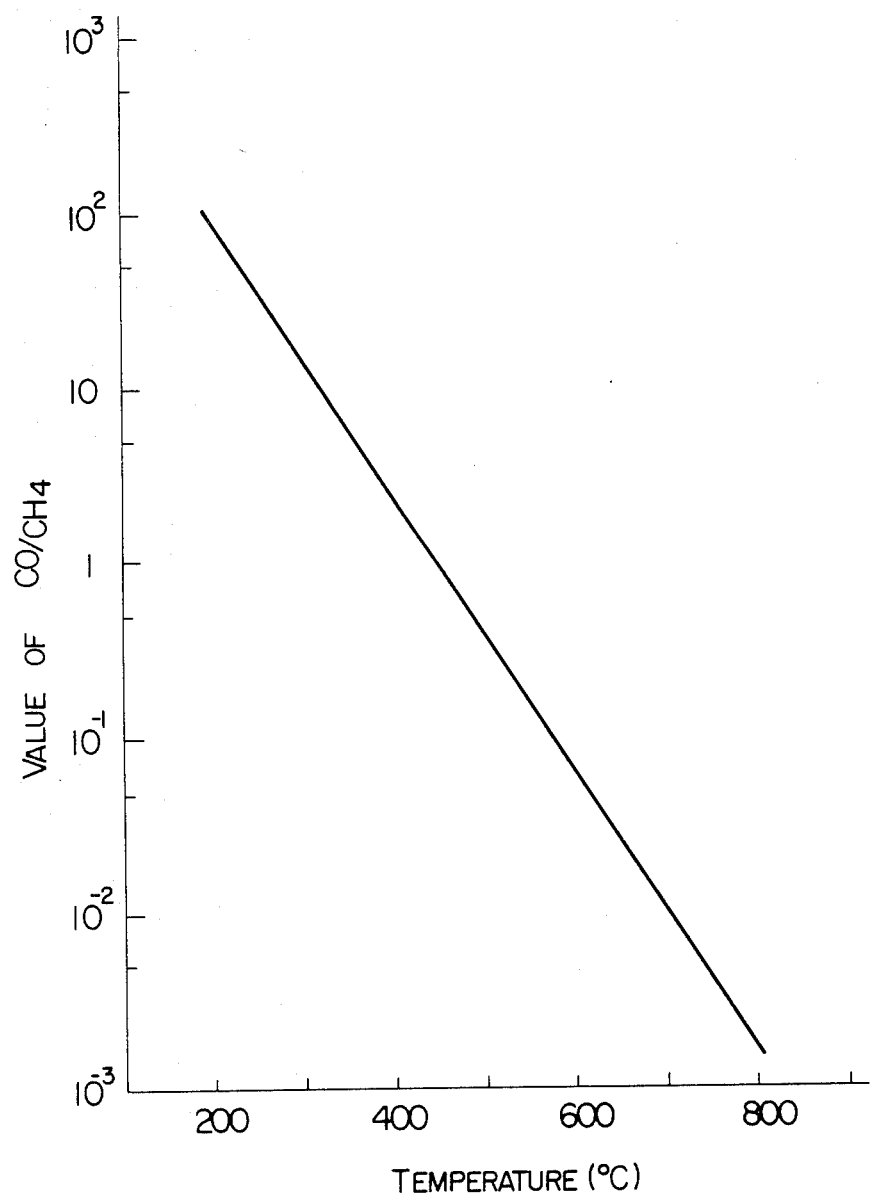
Figure 6:
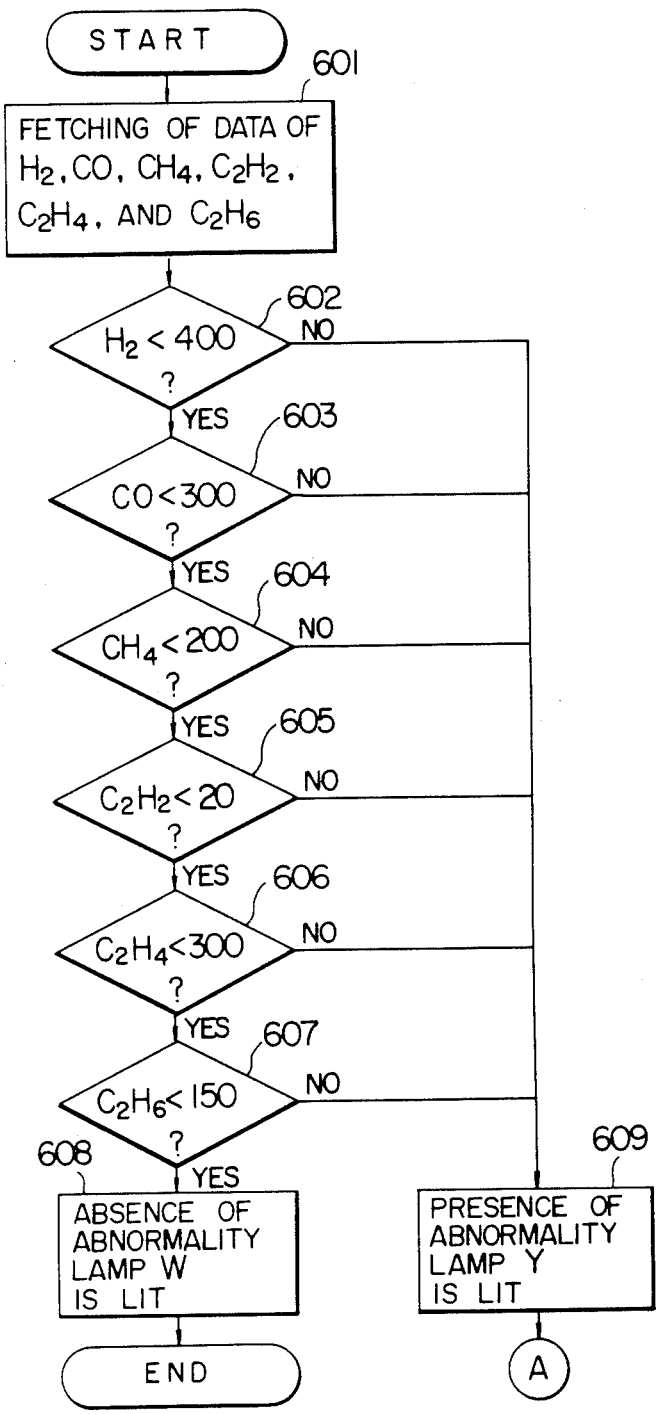
Figure 7:
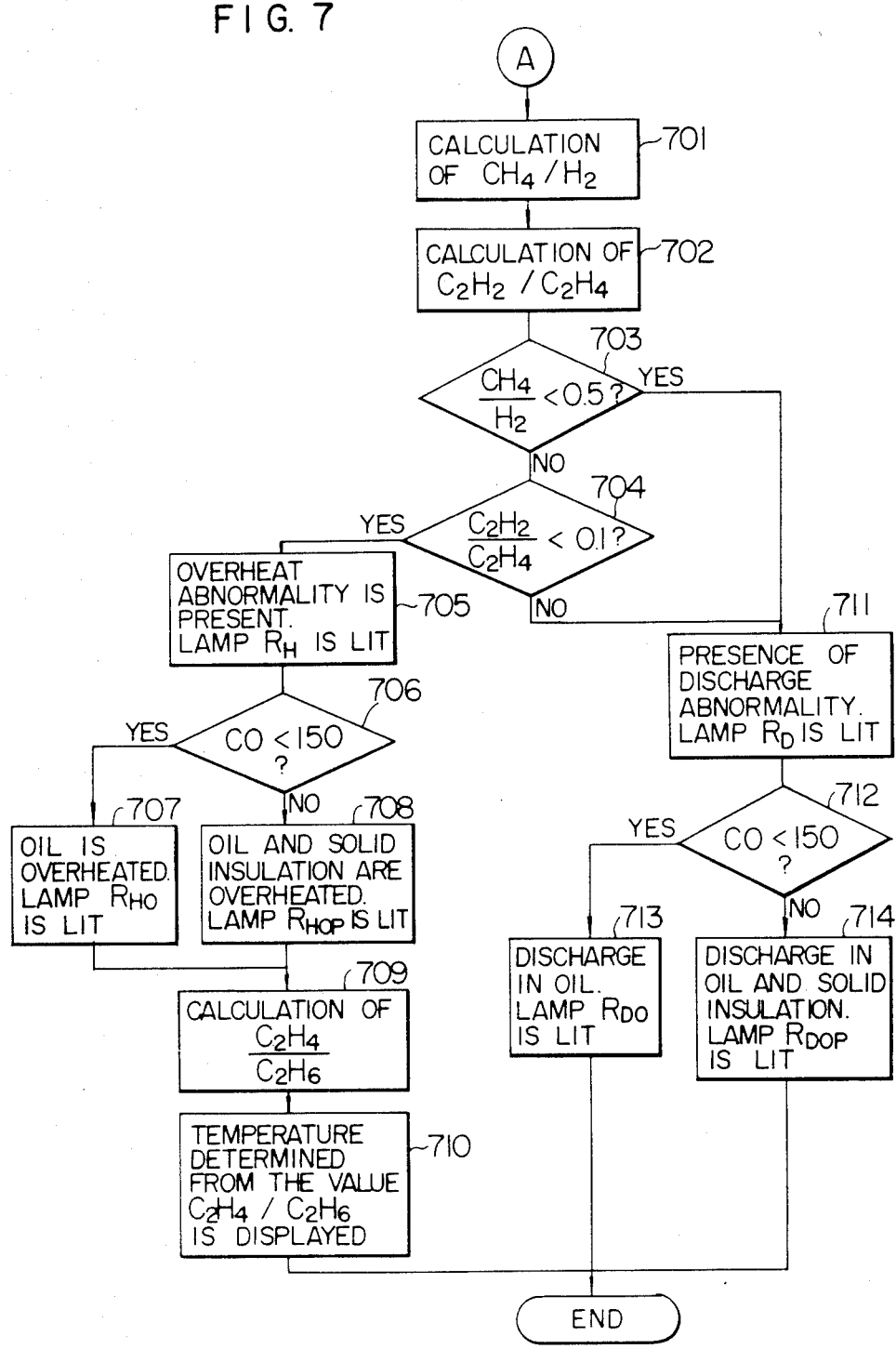
Figure 8:
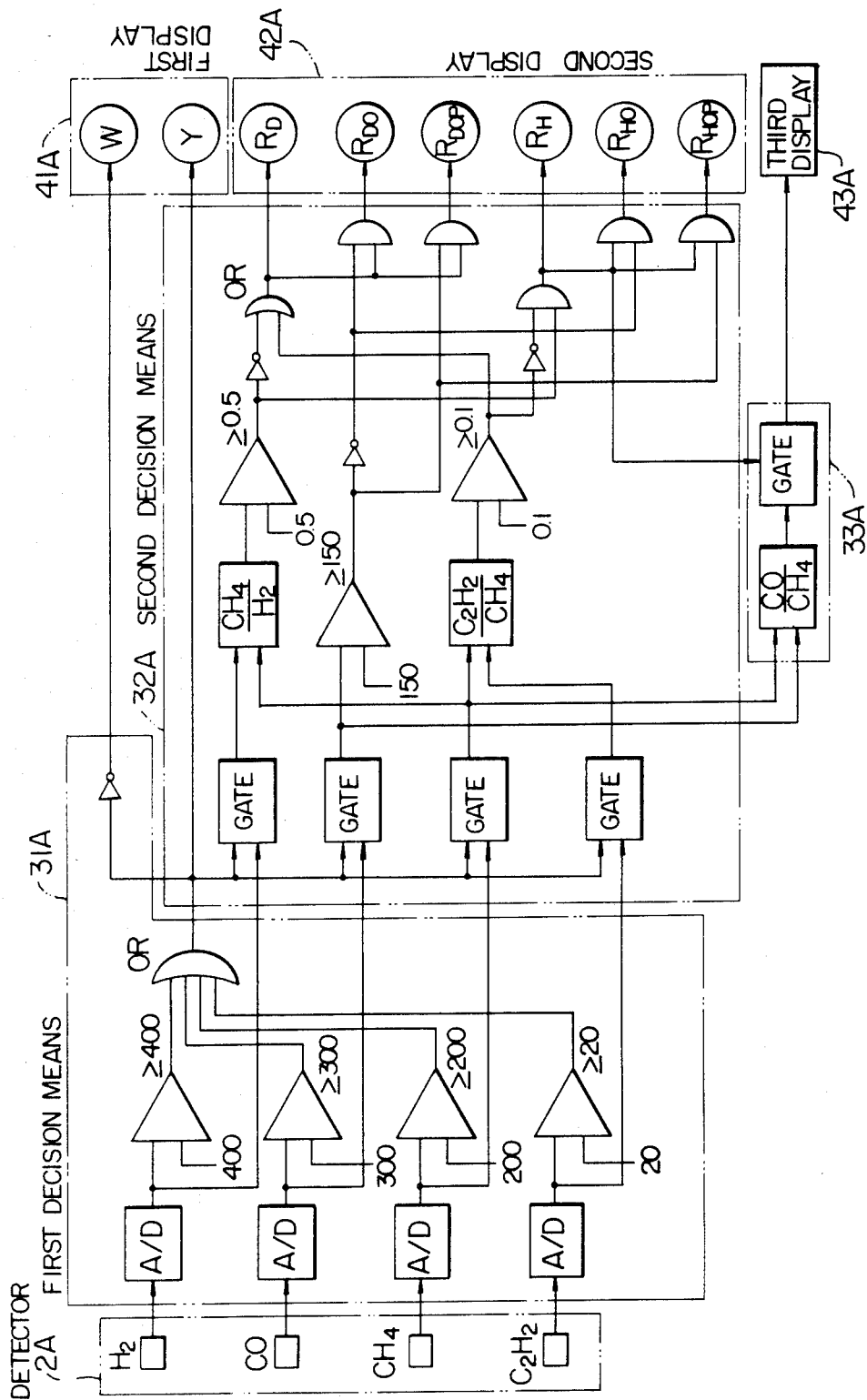
Figure 9:
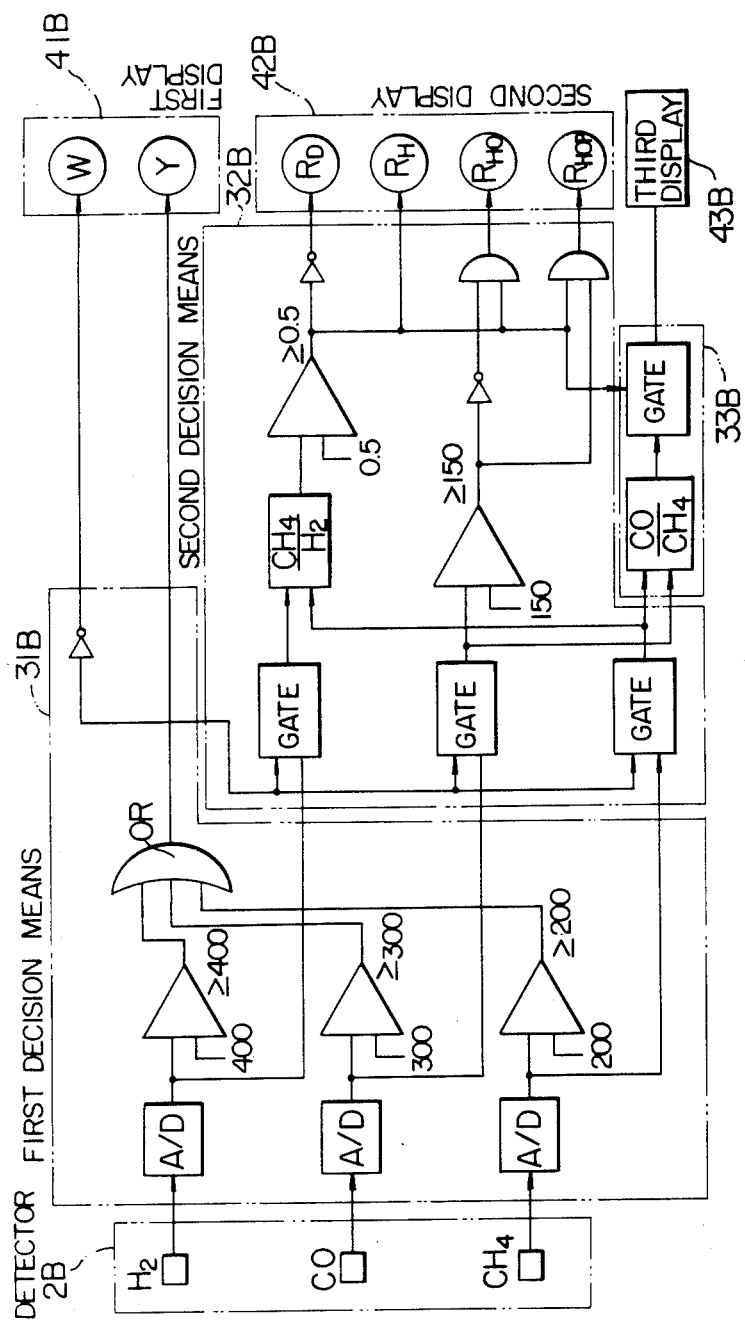

FIGS. 4 and 5 graphically illustrate a relationship between temperature of an overheated portion and the ratio of $C_2H_2/C_2H_6$ and $CO/CH_4$, respectively;

FIGS. 6 and 7 show flow charts illustrating processes for carrying out the invention with the aid of a microcomputer;

FIG. 8 shows a circuit diagram of the apparatus according to another embodiment of the invention; and FIG. 9 shows a circuit diagram of the apparatus according to a further embodiment of the invention.

In the first place, description will be made on a basic concept adopted in an abnormality diagnosing method for an oil-filled electric apparatus according to the invention. It is already known that occurrence of internal abnormality such as overheating or electric discharge in the electric apparatus such as power transformer filled with insulation oil of hydrocarbon series brings about changes in the amount of $C_2H_2$, $C_2H_6$ and the like contained in a gas extracted from the oil, and thus it is possible to judge the presence or absence of abnormality and the type of abnormality, if present, on the basis of changes in the contents of these components. According to the invention, in order to rapidly and accurately make such judging in a simple manner, the judging is carried out in two steps, i.e. the first step of deciding that the abnormality is present when the amount of any one of specifically selected components contained in the gas extracted from the oil exceeds a preset reference level and, if present, the second step of determining whether the abnormality is derived from electric discharge or overheating. When it is decided at the first step that no abnormality exists, the second step can be omitted. In the diagnosis at the second step, the determination of whether the abnormality is derived from electric discharge or overheat is made on the basis of the ratio of contents of two specific components which are very susceptible to the influence of the electric discharge and the overheat. In this connection, the inventors of the present application have studied various power transformers in which abnormality occurred actually, the results of which have showed that, when the ratio of $C_2H_2/C_2H_4$ or $C_2H_2/CH_4$ is selected as the ratio of the two specific components mentioned above, most of the values of that ratio lies in a range exceeding a certain threshold level when the abnormality is due to electric discharge, while most of the values of the ratio falls within a range smaller than the threshold level when the abnormality is due to overheat. Further, when the ratio of $CH_4/H_2$ is employed, it has been found that most of the values of this ratio lies in a range smaller than a certain threshold value in the case of the abnormality due to electric discharge, while they fall within a range greater than the threshold value in the case of the abnormality due to overheat. However, when the values of either the first mentioned ratio or the last mentioned one lie in the vicinity of the respective threshold levels, it is difficult to decide with reliability whether the abnormality is due to electric discharge or overheat, since both types of abnormality, if not so often, may give such values of any ratio as falling within the range in the vicinity of its threshold level. In view of the above, it is comtemplated with the invention that importance is put on the abnormality of electric discharge which is a prominent factor leading to serious damage of the electric apparatus, and that when the value of ratio $C_2H_2/C_2H_4$ or $C_2H_2/CH_4$ is employed, a reference value slightly smaller than the threshold level mentioned above is adopted, wherein decision of the discharge abnormality is made when the value of the above ratio is greater than the reference value. On the other hand, when the value of ratio $CH_4/H_2$ is employed, a reference value slightly greater than the threshold level mentioned above is used, wherein decision of the discharge abnormality is made in case the value of ratio $CH_4/H_2$ is smaller than the reference value. In this way, the missing in detection of the discharge abnormality, is avoided.

Further, in the decision of the second step, the location at which the abnormality occurs is determined on the basis of the content of CO, i.e. it is determined whether the abnormality occurs only in the insulation oil or over the insulation oil and a solid insulation such as insulating paper. When the second step decides that the abnormality is due to overheat, the prevailing temperature may be arithmetically determined on the basis of the value of ratio $C_2H_4/C_2H_6$ or $CO/CH_4$ which is closely related to the temperature of overheat, whereby more appropriate diagnosis can be made.

Figure 1:
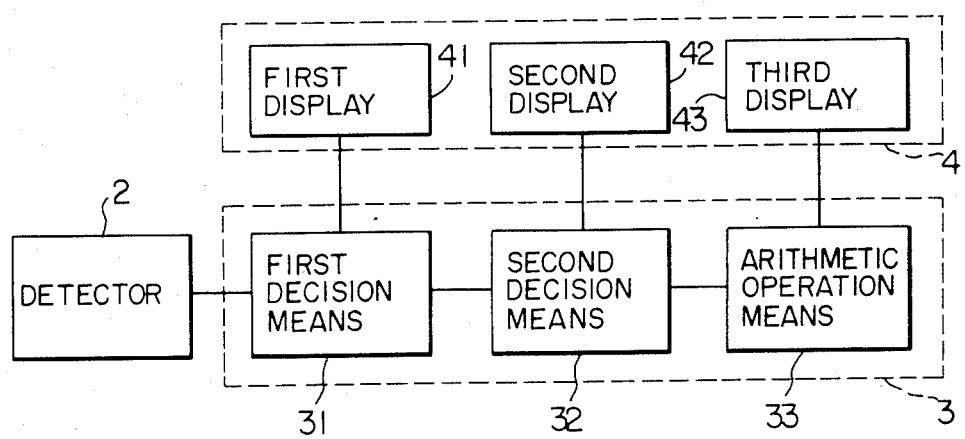
FIG. 1 shows a basic arrangement of an apparatus for carrying out the method according to the invention.

Next, referring to FIG. 1, there is shown a basic arrangement of an apparatus for carrying out the method according to the invention. In the figure, a reference numeral 2 denotes a sensor or detector device adapted to detect the contents of all or some of the components $H_2$, CO, $CH_4$, $C_2H_2$, $C_2H_4$ and $C_2H_5$ contained in the gas extracted from the oil in an oil-filled electric apparatus and produce corresponding signals at the outputs. Such sensor device may be constituted by a detector disclosed in U.S. patent application Ser. No. 265,656 filed May 20, 1981 now U.S. Pat. No. 4,402,211 entitled "System for Monitoring Abnormality of Oil-filled Electric Device". A reference numeral 3 denotes a decision making or processing unit including a first decision means 31 which is so arranged as to compare the contents of the gas components mentioned above with respective reference values preset for the gas components and decide that the electric apparatus is in the normal state when the contents of all the gas components do not exceed the respective reference values. On the contrary, when the content of any one of the gas components does exceed the associated reference value, the first decision means 31 determines that abnormality exists within the oil-filled electric apparatus. The decision making or processing unit 3 further includes second decision means 32 which responds to the output of the first decision means 31 indicating the presence of abnormality and determines the type of the abnormality on the basis of the ratio in contents of at least one set of two specific components and additionally determines whether the abnormality as detected is involved only in the insulation oil or over both the insulation oil and the solid insulation. In succession to the second decision means 32, there is disposed an arithmetic operation means 33 for arithmetically determining the temperature of overheat from the ratio of two specific components, when the overheat abnormality is detected by the second decision means 32. A reference numeral 4 denotes a display device for displaying the results obtained by the decision processing unit 3. The display device 4 includes a first display means 41 for displaying the result of the decision made by the first decision means 31 as to the presence or absence of abnormality, a second display means 42 for displaying the result of decision made by the second decision means 32 as to the type of the abnormality and location where the abnormality occurs (e.g. discharge in oil, discharge over oil and solid insulation, overheat of oil, overheat over oil and solid insulation), and a third display means 43 for displaying the result of the arithmetic operation outputted from the arithmetic operation means 33.

Figure 2:
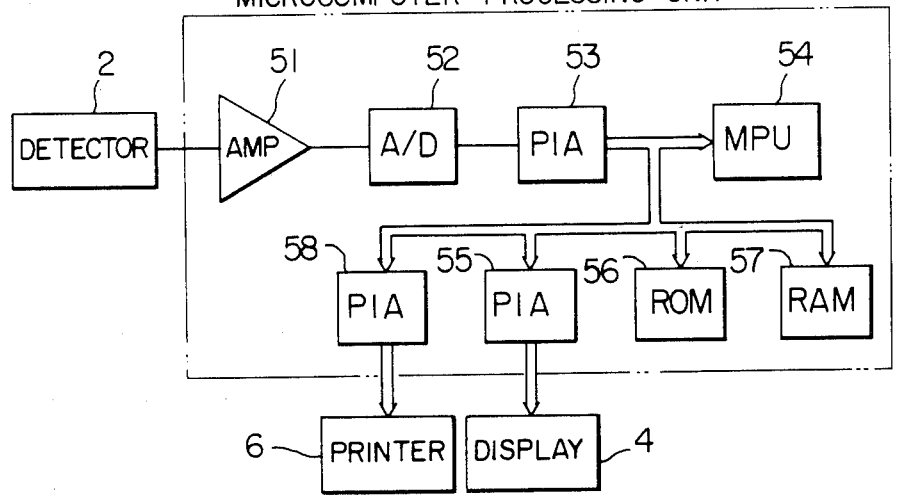
FIG. 2 is a view showing a basic arrangement of an apparatus for carrying out the method according to the invention with the aid of a microcomputer.

The method according to the invention can also be carried out through software technique by using a microcomputer. A basic circuit arrangement suited to this end is shown in FIG. 2, by way of example. In this figure, the detecting device 2 and the display device 4 are same as those shown in FIG. 1. However, a microcomputer processing unit 5 is provided in place of the decision processing unit 3 shown in FIG. 1. The computer processing unit 5 includes an amplifier 51 adapted to receive and amplify the signals successively produced from the output of the detector or sensor device 2 and representing the contents of the various gas components mentioned hereinbefore, an A/D converter 52 for cnverting sequentially analog outputs from the amplifier 51 into digital signals, and a microcomputer system including an input interface 53, a microcomputer 54, a read-only memory or ROM 56, a random access memory or RAM 57 and an output interface 55 to receive the digital signals mentioned above and process them in accordance with a predetermined program, the result of the processing being displayed by the display unit 4. This processing will be described in detail later on.

Figure 3:
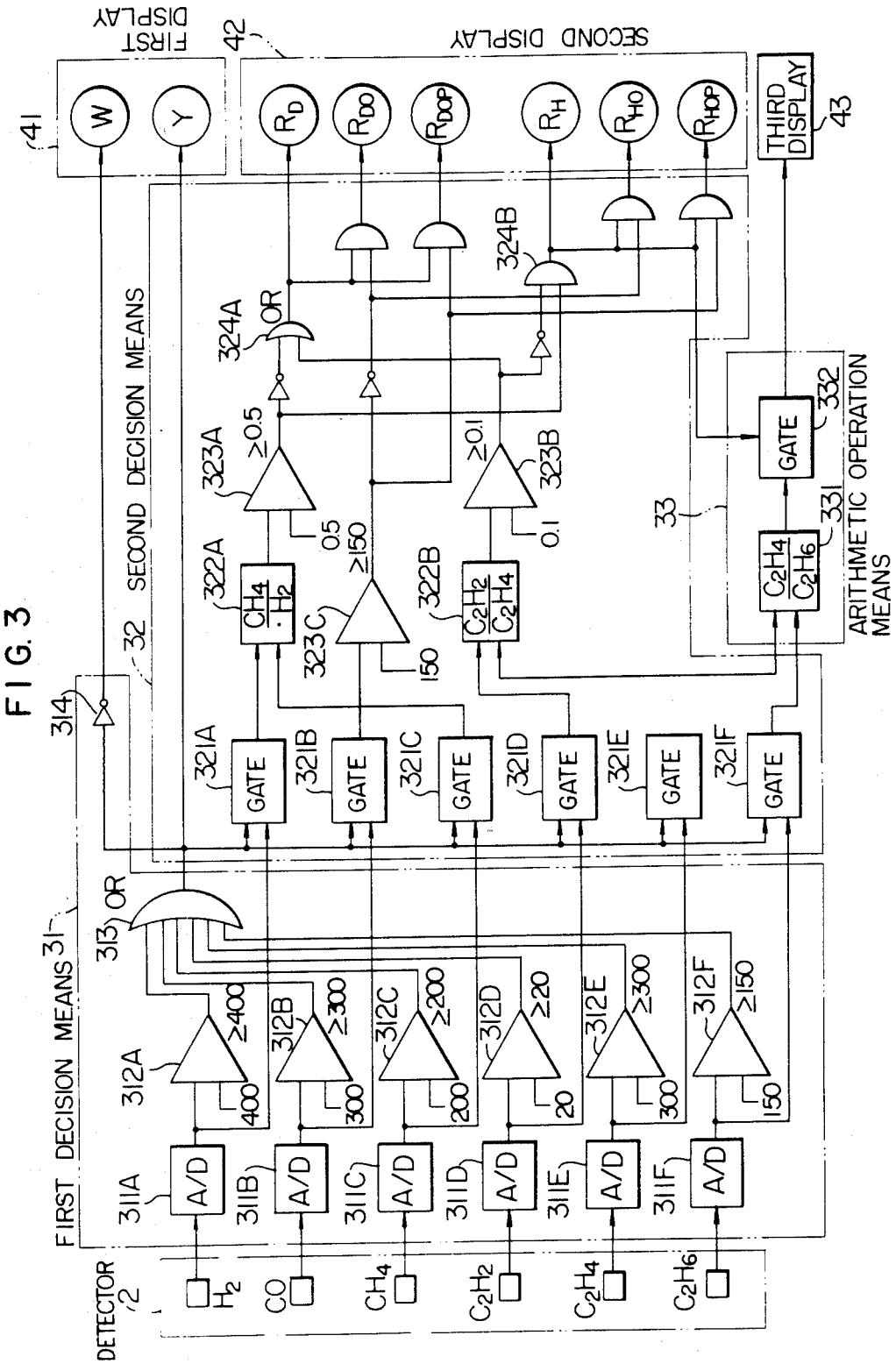
FIG. 3 shows in detail a circuit diagram of the apparatus structured according to the basic arrangement of FIG. 1.

FIG. 3 shows in detail a circuit arrangement of the unit for diagnosing the abnormality on the basis of the contents of six components, $H_2$, CO, $CH_4$, $C_2H_2$, $C_2H_4$ and $C_2H_6$ in accordance with the basic concept illustrated in FIG. 1. The detector 2 is of the type disclosed in the aforementioned copending U.S. application Ser. No. 265,656 and adapted to output sequentially electric signals representative of the contents of $H_2$, CO, $CH_4$, $C_2H_2$, $C_2H_4$ and $C_2H_6$ in a predetermined order. These electrical signals are supplied to A/D converters 311A to 311F of the first decision means 31 through a conventional distributor circuit (not shown) to be thereby converted into digital signals. The digital signals are then compared with reference values respectively preset for the components through comparators 312A, ..., 312F, respectively.

In the case of the illustrated embodiment, the reference values mentioned below are used for the individual components. When contents of all the components are smaller than the respective reference values, it is decided that no abnormality is present. On the other hand, when the content of any one of the components is equal to or greater than the corresponding reference value, the presence of abnormality is determined.

$H_2$: 400 ppm
CO: 300 ppm
$CH_4$: 200 ppm
$C_2H_2$: 20 ppm
$C_2H_4$: 300 ppm
$C_2H_6$: 150 ppm In more particular, the comparator 312A compares the digital signal supplied from the A/D converter 311A and representing the content of $H_2$ with the reference value of 400 (ppm) and produces logic "1" signal when $H_2 \geq 400$, while producing logic "0" when $H_2 < 400$. In similar manner, the comparators 311B, 311C, 311D, 311E and 311F produce logic "1" signals, when $CO \geq 300$, $CH_4 \geq 200$, $C_2H_2 \geq 20$, $C_2H_4 \geq 300$ and $C_2H_6 \geq 150$, respectively. The output signals from these comparator are supplied to the input of an OR gate 313 which produces logic "0" when all the input signals are logic "0", and produces logic "1" when any one of the input signals is logic "1". In other words, the output signal of logic "1" produced by the OR gate 313 indicates the abnormality, resulting in that a yellow lamp Y of the first display device 41 is energized to give the indication of abnormality. On the other hand, the output signal of logic "0" from the OR gate 313 indicates that no abnormality is present. This signal of logic "0" is inverted to a signal of logic "1" by an inverter 314 and utilized to light a white lamp W indicating the absence of abnormality.

When the decision that no abnormality is present is issued, the processing is then terminated. However, when the decision indicative of the presence of abnormality is issued, the second decision means 32 is then activated. Namely, gate circuits 321A, 321B, 321C, 321D, 321E and 321F of the second decision means 32 are enabled by the signal of logic "1" outputted from the OR gate 313, whereby the digital signals representing the contents of the individual components, respectively, are fetched by the second decision means 32, which determines the type of abnormality and the location where the abnormality occurs by comparing the ratios $CH_4/H_2$ and $C_2H_2/C_2H_4$ and the content of CO with respective reference values. In the case of the illustrated embodiment, determination of the type of abnormality is made in accordance with the following table I.

TABLE I

| Type of Abnormality | $\dfrac{CH_4}{H_2}$ | | $\dfrac{C_2H_2}{C_2H_4}$ | |
|---|---|---|---|---|
| | $\geq 0.5$ | $<0.5$ | $\geq 0.1$ | $<0.1$ |
| Electric Discharge | | o | o | |
| | o | | | o |
| | | | o | |
| Overheat | o | | | o |

As will be appreciated, when either one of the condition that $CH_4/H_2 < 0.5$ and the condition that $C_2H_2/C_2H_4 \geq 0.1$ is fulfilled, decision is made to the effect that the abnormality is brought about by the electric discharge. On the other hand, when both of the conditions that $CH_4/H_2 \geq 0.5$ and that $C_2H_2/C_2H_4 < 0.1$ are met, it is decided that the abnormality is due to overheat. In this way, greater importance is put on the discharge abnormality, whereby the occurrence of the discharge is determined when there exists even a bit of probability of discharge. To this end, divider circuits 322A and 322B arithmetically determine the values of the ratios $CH_4/H_2$ and $C_2H_2/C_2H_4$, respectively, which values are compared with the respective reference values 0.5 and 0.1 through comparators 323A and 323B, rspectively. These comparators produce output signals of logic "1", when $CH_4/H_2 \geq 0.5$ and $C_2H_2/C_2H_4 \geq 0.1$, respectively. The output signals from the comparators 323A and 323B are utilized to light a discharge indicating red lamp $R_D$ of the second display 42 through an OR gate 324A and an AND gate 324B respectively, when the discharge is determined in accordance with the conditions listed in the table I, while these output signals are utilized for lighting an overheat indicating red lamp $R_H$ when the overheat abnormality is determined.

Further, the content of CO is compared with the reference value of 150 (ppm) by a comparator 323C. When $CO \geq 150$, it is decided that the abnormality occurs over oil and solid insulation, whereby either a red lamp $R_{DOP}$ or $R_{HOP}$ of the second display 42 is energized in dependence on whether the abnormality due to the discharge or the overheat. On the other hand, when $CO < 150$, it is decided that the abnormality is confined only to the oil, and either a red lamp $R_{DO}$ or $R_{HO}$ is lit in dependence on whether the abnormality is due to discharge or the overheat.

In case the overheat abnormality is determined, a gate 332 of the arithmetic operation means 33 is enabled by the output signal from the AND gate 324B, whereby the value of $C_2H_4/C_2H_6$ calculated by a divider circuit 331 is supplied to the display device 43. On the basis of the input value of $C_2H_4/C_2H_6$, the display device 43 displays the temperature of the overheated portion in accordance with a relation depicted in FIG. 4.

In this connection, it should be mentioned that the temperature of the overheated portion may be determined from the ratio of $CO/CH_4$. In this case, the temperature can be determined in accordance with a relation between $CO/CH_4$ and the temperature depicted in FIG. 5.

The processing performed by the circuit shown in FIG. 3 may also be executed by the computer system shown in FIG. 2 in the similar manner. Processing programs for this processing are shown in flow charts of FIGS. 6 and 7.

FIG. 6 illustrates a first decision routine. At first, the contents of $H_2$, CO, $CH_4$, $C_2H_2$, $C_2H_4$ and $C_2H_6$ are fetched at a step 601. In other words, the signals produced by the detector 2 shown in FIG. 2 and representing the contents of these components, respectively, are successively amplified by the amplifier 51 and converted into digital signals by the A/D converter 52. At a step 601, the digital signals are successively fetched through the input interface 53 to be stored in the RAM 57. The signals representative of the contents of the components are sequentially compared with the respective reference values at steps 602 to 607. When the content of any component is found to be equal to or greater than the corresponding reference value at any one of these steps 602 to 607, the processing immediately proceeds to a step 609 at which the yellow lamp Y is lit, indicating the abnormality, whereupon the second decision routine is initiated. On the other hand, when the contents of all the components are found smaller than the respective reference values, a step 608 is reached, whereby the white lamp W for indicating the absence of abnormality is lit. The processing is then terminated.

The second decision routine illustrated in FIG. 7 includes the steps 701 to 704 where the ratios $CH_4/H_2$ and $C_2H_2/C_2H_4$ are calculated and compared with the respective reference values 0.5 and 0.1, the steps 711 to 714 where the abnormality due to electric discharge is determined when either the condition that $CH_2/H_2<0.5$ or $C_2H_2/C_2H_4 \geqq 0.1$ is met, to thereby light the lamp $R_D$ and then the location at which the abnormality occurs is determined on the basis of the value of CO to thereby lit the associated lamp, and the steps 705 to 710 at which the abnormality due to overheat is determined when both of the conditions that $CH_4/H_2 \geqq 0.5$ and that $C_2H_2/C_2H_4$ are met, to thereby light the lamp $R_H$. In the course of execution of these steps 705 to 710, the location of the abnormality is also determined on the basis of the content of CO to thereby energize the assocated lamps, while the temperature of the overheated location is additionally determined from the value of the ratio $C_2H_4/C_2H_6$.

It should be noted that the contents of the individual components regardless of the presence or absence of abnormality and additionally, the value of the calculated ratio of each set of two components upon detection of the presence of abnormality may be recorded by a printer 6 through the interface 58, as shown in FIG. 2, before the end of the processing.

Further, in the above-mentioned embodiment, the values of $C_2H_2/C_2H_4$ and $CH_4/H_2$ are used for determining whether the abnormality is due to electric discharge or overheat. Alternatively, the values of $CH_4/H_2$ and $C_2H_2/C_2H_6$ may be used for the purpose, although the reference values for the ratios of $CH_4/H_2$ and $C_2H_2/C_2H_6$ should be experimentally determined.

Next, description will be made as to the manner in which the method according to the invention is really applied to the diagnosis of oil-filled electric apparatus for the contents of the various components listed in Table II which wear actually measured for various power transformers rated 1 MVA or higher. The data in Examples Nos. 2 to 5 were obtained from transformers which were actually subjected to abnormality.

TABLE II

| | (by ppm) | | | | | |
|---|---|---|---|---|---|---|
| | Gas Components | | | | | |
| Example Nos. | $H_2$ | CO | $CH_4$ | $C_2H_2$ | $C_2H_4$ | $C_2H_6$ |
| 1 | 58 | 183 | 18 | 3 | 12 | 2 |
| 2 | 423 | 37 | 30 | 59 | 11 | 29 |
| 3 | 446 | 166 | 93 | 637 | 145 | 7 |
| 4 | 518 | 99 | 1179 | 6 | 2272 | 273 |
| 5 | 627 | 219 | 2422 | 7 | 2302 | 663 |

EXAMPLE 1

Since the level check effected at the steps 602 to 607 has proved that none of the six components exceeds the predetermined reference contents, the processing proceeds to the step 608 where the absence of abnormality is indicated. The power transformer is diagnosed to be free of any abnormality.

EXAMPLE 2

At the level check step 602, it is found that the content of $H_2$ exceeds the reference value thereof. The processing proceeds to the step 609 where the presence of abnormality is displayed. Subsequently, at the step 704, it is determined that $CH_4/H_2<0.5$. Although $C_2H_2/CH_4>0.1$, the step 711 is executed to determine the discharge abnormality. Further, the step 712 has proven that CO<150 (ppm). Accordingly, indication is made at the step 713 such that the discharge occurs in oil. Thus, it is diagnosed that discharge takes place in oil, which discharge is irrelevant to the solid insulation.

EXAMPLE 3

In this case, both contents of $H_2$ and $C_2H_2$ exceed the respective reference values. At the step 602, it is determined that the content of $H_2$ exceeds the predetermined reference value, resulting in that the indication of abnormality is produced at the step 609. Next, at the step 703, it is found that $CH_4/H_2<0.5$. Accordingly, the step 711 is executed (notwithstanding the fact that $C_2H_2/CH_4>0.1$), whereby indication of the discharge is displayed. Further, it is detected at the step 712 that CO>150 (ppm), resulting in that the discharge takes place in both oil and solid insulation at the step 714. Thus, it is diagnosed that discharge has occurred in oil associated with solid insulation.

EXAMPLE 4

In this case, the contents of $H_2$, $CH_4$, $C_2H_4$ and $C_2H_6$ exceeds the respective reference levels. At the step 609, it is detected that the content of $H_2$ exceeds the corresponding reference value, as the result of which the indication of abnormality is displayed at the step 609. Next, when it is detected at the step 703 that $CH_4/H_2>0.5$, indication of the overheat abnormality is displayed at the step 704 because $C_2H_2/C_2H_4<0.1$. Further, it is determined at the step 706 that CO<150 (ppm), resulting in that the overheat of oil is indicated at the step 707. At the step 709, it is arithmetically determined that $C_2H_2/C_2H_6=8.32$, whereby the temperature of the overheated oil portion is determined to be 810° C. from the relation illustated in FIG. 4. Thus, it is diagnosed that abnormal overheating has occurred in oil associated with solid insulation in the transformer, and that the temperature of the overheated portion is 810° C.

EXAMPLE 5

In this case, all the components except for $C_2H_2$ exceed the respective reference levels. As the result of the level check of $H_2$ at the step 602, the abnormality indication is displayed at a step 609. At the next step 703, it is detected that $CH_4/H_2 > 0.5$, resulting in that indication of the overheat is displayed at the step 705 because $C_2H_2/C_2H_4 < 0.1$. Further, it is determined at the step 706 that $CO > 150$ (ppm), whereby the overheat of solid insulation is displayed at the step 708. Further, the ratio $C_2H_4/C_2H_6$ is calculated to be equal to 3.47. The temperature of the overheated portion is determined to be 710° C. from the relation illustrated in FIG. 5. Thus, the result of the diagnosis is that the abnormal overheating has occurred in oil associated with solid insulation at the temperature of 710° C. in the oil transformer.

The above examples illustrate application of the inventive method to the diagnoses of the oil-filled electric apparatus such as the oil transformers. It has been found that the results of the diagnoses substantially coincide with the results of the internal inspections actually conducted for the diagnosed transformers. Thus, it is safe to say that the diagnosis method according to the invention is satisfactorily reliable.

FIGS. 8 and 9 show other embodiments of the apparatus for carrying out the method according to the invention. The circuit arrangement conforms to the basic concept illustrated in FIG. 1 and differs from the embodiment shown in FIG. 3 in that the number of the gases to be detected is reduced, to thereby simplify correspondingly the circuit configuration.

In the case of the embodiment shown in FIG. 8, four gas components $H_2$, $CO$, $CH_4$ and $C_2H_2$ are detected. The reference values employed for the level check or comparison of these components are same as those employed in the embodiment shown in FIG. 3. For determination of the type of abnormality, the ratios $CH_4/H_2$ and $C_2H_2/CH_4$ are compared with the corresponding reference values of 0.5 and 0.1, respectively. When either one of the conditions that $CH_4/H_2 < 0.5$ or $C_2H_2/CH_4 \geq 0.1$ is met, it is determined that the abnormality due to electric discharge occurs. On the other hand, when both conditions that $CH_4/H_2 \geq 0.5$ and that $C_2H_2/CH_4 < 0.1$ are met, then it is decided that the overheat abnormality does occur. The temperature of the overheat is determined from the value of $CO/CH_4$ in accordance with relation illustrated in FIG. 5.

In the case of the embodiment shown in FIG. 9, three gas components $H_2$, $CO$ and $CH_4$ are detected. The level checks or comparisons of these components are effected in the manner similar to the embodiment shown in FIG. 3. Determination of the type of abnormality is made only from the ratio of $CH_4/H_2$. When $CH_4/H_2 \geq 0.5$, it is determined that the overheat abnormality occurs. When $CH_4/H_2 < 0.5$, the discharge abnormality is detected. Determination of the location at which the abnormality prevails as well as the calculation of the temperature of the overheated portion are processed in the manner similar to the embodiment shown in FIG. 8.

It should be appreciated that the various reference values mentioned in the foregoing are only for the purpose of exemplary illustration. Needless to say, these reference values may be selected optimal in consideration of the type of the electric apparatus to which the invention are applied, precision of the detectors for the various gas components and other factors.

As will be appreciated from the foregoing description, the abnormality diagnosis according to the invention is carried out at two stages, that is, the stage for determining the presence or absence of abnormality through the level check of the contents of plural gas components extracted from oil in an oil-filled electrical apparatus and the stage for determining the type of abnormality, if present, on the basis of the content ratio of at least one set of two specific components. By virtue of this feature, the diagnosis can be made with a high accuracy in a simple manner. Further, the diagnosis system is easy to be automatized and can be incorporated in a portable apparatus. Accordingly, when the detectors for detecting the in-oil gases such as disclosed in the aforementioned copending U.S. patent application Ser. No. 265,656 are preliminarily mounted in the power transformers to be monitored, the operator can inspect them in their situations for abnormality by the portable diagnosis apparatus.

What we claim is:

1. A method of diagnosing an oil-filled electric apparatus as to abnormality, comprising steps of:
    detecting contents of a plurality of predetermined components contained in gas extracted from oil of said electric apparatus, said components bearing relevance to abnormality of said electric apparatus due to electric discharge and overheat;
    determining the presence or absence of abnormality due to electric discharge or overheat by comparing the contents of said gas components with respective reference values;
    determining the ratio of contents for at least one set of two selected components among those detected, when the presence of abnormality has been determined, and determining on the basis of the value of said ratio whether said abnormality is due to overheat or discharge; and
    further including a step of arithmetically determining the temperature of overheat, if the abnormality is due to overheat, on the basis of ratio of the contents of selected two of said components.

2. A diagnosing method according to claim 1, wherein said components detected are $H_2$, $CO$, $CH_4$, $C_2H_2$, $C_2H_4$ and $C_2H_6$.

3. A diagnosing method according to claim 2, wherein determination as to whether the abnormality is due to overheat or discharge is made by comparing ratios of $CH_4/H_2$ and $C_2H_2/C_2H_4$ with respective predetermined reference values.

4. A diagnosing method according to claim 2, wherein determination as to whether the abnormality is due to overheat or discharge is made by comparing ratios of $CH_4/H_2$ and $C_2H_2/CH_4$ with respective predetermined reference values.

5. A diagnosing method according to claim 2, wherein determination as to whether the abnormality is due to overheat or discharge is made by comparing the ratio of $CH_4/H_2$ with a predetermined reference value.

6. A diagnosing method according to any one of claims 1 and 2 to 5, further including a step for determining whether the abnormality occurs in oil and solid insulator or only in oil by comparing the content of CO with a predetermined reference value.

7. A diagnosing method according to claim 1, wherein the contents of $C_2H_4$ and $C_2H_6$ are detected, and wherein the ratio of contents of said two components used for said arithmetically determining step is $C_2H_4/C_2H_6$.

8. A diagnosing method according to claim 1, wherein the contents of $CO$ and $CH_4$ are detected, and wherein the ratio of contents of said two components used for said arithmetically determining step is $CO/CH_4$.

9. A diagnosing method according to claim 1, wherein said components detected are $H_2$, $CO$, $CH_4$ and $C_2H_2$.

10. A diagnosing method according to claim 9, wherein determination as to whether the abnormality is due to overheat or discharge is made by comparing ratios of $CH_4/H_2$ and $C_2H_2/CH_4$ with respective predetermined reference values.

11. A diagnosing method according to claim 9, wherein determination as to whether the abnormality is due to overheat or discharge is made by comparing the ratio of $CH_4/H_2$ with a predetermined reference value.

12. A diagnosing method according to claim 1, wherein said components detected are $H_2$, $CO$ and $CH_4$.

13. An apparatus for diagnosing an oil-filled electric apparatus as to abnormality, comprising:
   first means receiving signals representing contents of a plurality of predetermined components contained in gas extracted from oil of said electric apparatus, said components bearing relevance to abnormality of said electric apparatus due to electric discharge and overheat;
   second means for determining the presence or absence of abnormality due to discharge or overheat by comparing the contents of said gas components with respective reference values;
   third means for obtaining ratio of contents for at least one set of two specific components among said components, when the presence of abnormality has been determined, thereby to determine on the basis of the value of the ratio whether said abnormality is due to overheat or discharge; and
   further including means for arithmetically determining the temperature of the overheat, if determined to be present, on the basis of ratio of contents of selected two of said components.

14. An apparatus for diagnosing an oil-filled electric apparatus according to claim 13, wherein said components are $H_2$, $CO$, $CH_4$, $C_2H_2$, $C_2H_4$ and $C_2H_6$.

15. An apparatus for diagnosing an oil-filled electric apparatus according to claim 14, wherein said third means includes means for comparing ratios of $CH_4/H_2$ and $C_2H_2/C_2H_4$ with respective predetermined reference values for determination of whether the abnormality is due to overheat or discharge.

16. An apparatus for diagnosing an oil-filled electric apparatus according to claim 14, wherein said third means includes means for comparing ratios of $CH_4/H_2$ and $C_2H_2/C_2H_6$ with respective predetermined reference values for determination of whether the abnormality is due to overheat or discharge.

17. An apparatus for diagnosing an oil-filled electric apparatus according to claim 14, wherein said third means includes means for comparing ratios of $CH_4/H_2$ and $C_2H_2/CH_4$ with respective predetermined reference values for determination of whether the abnormality is due to overheat or discharge.

18. An apparatus for diagnosing an oil-filled electric apparatus according to claim 14, wherein said third means includes means for comparing ratio of $CH_4/H_2$ with a predetermined reference value for determination of whether the abnormality is due to overheat or discharge.

19. An apparatus for diagnosing an oil-filled electric apparatus according to any one of claims 13 and 14 to 18, further including fourth means for determining whether the abnormality occurs in oil and solid insulator or only in oil by comparing the content of CO with a predetermined reference value.

20. An apparatus for diagnosing an oil-filled electric apparatus according to claim 13, wherein the first means receives signals representing contents of $C_2H_4$ and $C_2H_6$, and wherein the ratio of contents of said two components used for said arithmetically determining step is $C_2H_4/C_2H_6$.

21. An apparatus for diagnosing an oil-filled electric apparatus according to claim 13, wherein the first means receives signals representing contents of $CO$ and $CH_4$, and wherein the ratio of contents of said two components used for said arithmetically determining step is $CO/CH_4$.

22. An apparatus for diagnosing an oil-filled electric apparatus according to claim 13, wherein said components are $H_2$, $CO$, $CH_4$ and $C_2H_2$.

23. An apparatus for diagnosing an oil-filled electric apparatus according to claim 22, wherein said third means includes means for comparing ratios of $CH_4/H_2$ and $C_2H_2/CH_4$ with respective predetermined reference values for determination of whether the abnormality is due to overheat or discharge.

24. An apparatus for diagnosing an oil-filled electric apparatus according to claim 22, wherein said third means includes means for comparing ratio of $CH_4/H_2$ with a predetermined reference value for determination of whether the abnormality is due to overheat or discharge.

25. An apparatus for diagnosing an oil-filled electric apparatus according to claim 13, wherein said components are $H_2$, $CO$ and $CH_4$.

* * * * *